(12) United States Patent
Kuhrts

(10) Patent No.: US 8,609,154 B2
(45) Date of Patent: *Dec. 17, 2013

(54) ANTI-INFLAMMATORY CYCLOOXYGENASE INHIBITORS

(75) Inventor: Eric H. Kuhrts, Bodega, CA (US)

(73) Assignee: Metaproteomics, LLC, Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/448,623

(22) Filed: Apr. 17, 2012

(65) Prior Publication Data

US 2012/0270951 A1    Oct. 25, 2012

Related U.S. Application Data

(63) Continuation of application No. 10/008,778, filed on Nov. 13, 2001, now Pat. No. 8,158,160.

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS

| | | |
|---|---|---|
| 3,451,821 A | 6/1969 | Todd et al. |
| 3,536,495 A | 10/1970 | Westermann et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,590,296 A | 5/1986 | Cowles et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Stegnik et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,919,813 A | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcera |
| 6,482,456 B1 | 11/2002 | Yokoo et al. |
| 6,492,429 B1 | 12/2002 | Graus et al. |
| 6,583,322 B1 | 6/2003 | Shalai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,078,062 B2 | 7/2006 | Hass |
| 7,144,590 B2 | 12/2006 | Khurts |
| 7,195,785 B2 | 3/2007 | Babish et al. |
| 7,205,151 B2 | 4/2007 | Babish et al. |
| 7,270,835 B2 | 9/2007 | Tripp et al. |

(Continued)

FOREIGN PATENT DOCUMENTS

| | | |
|---|---|---|
| CN | 1203268 | 12/1998 |
| DE | 1901277 | 8/1970 |

(Continued)

OTHER PUBLICATIONS

Abel-salam et al., Pharmacological Research, England 47(4), pp. 311-340 (Apr. 2003).

Albal, MV., et al., "Clinical evaluation of berberine in mycotic infections." Indian J. Ophthalmol 34:91-2 (1986).

Anto, et al., "Anti-inflammatory Activity of Natural and Synthetic Curcuminoids", Pharmacy and Pharmacology Communications, 4(2), pp. 103-106 (1998).

Baldermann et al., J. Chromatography A 1192(1):191-3 (May 23, 2008) (Epub Apr. 8, 2008); abstract only (1 page).

Bermejo, et al. Rev. Esp. Enferm. Dig. 95(9): 621-624 and 625-628 (2003).

(Continued)

*Primary Examiner* — Michael Meller
(74) *Attorney, Agent, or Firm* — McDermott Will & Emery LLP

(57) ABSTRACT

Disclosed is a pharmaceutical composition including a therapeutic quantity of a COX-2 inhibitor having an IC50-WHMA COX-2/COX-1 ratio ranging from about 0.23 to about 3.33 with reduced gastrointestinal and cardiovascular toxicity. Also disclosed are methods for treating osteoarthritis, rheumatoid arthritis or acute pain with less side-effects and faster onset of action utilizing the disclosed pharmaceutical composition.

1 Claim, No Drawings

(56) References Cited

U.S. PATENT DOCUMENTS

| | | |
|---|---|---|
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0003212 A1 | 1/2003 | Chien et al. |
| 2003/0008021 A1 | 1/2003 | Babish et al. |
| 2003/0035851 A1 | 2/2003 | Chen |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1 | 9/2003 | Jia et al. |
| 2003/0228369 A1 | 12/2003 | Kuhrts |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0151792 A1 | 8/2004 | Tripp et al. |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0074052 A1 | 4/2006 | Eliaz |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 | 10/2006 | Yajima et al. |
| 2007/0003646 A1 | 1/2007 | Kuhrts |
| 2007/0020352 A1 | 1/2007 | Tripp et al. |
| 2007/0065456 A1 | 3/2007 | Woods |
| 2007/0154576 A1 | 7/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |
| 2009/0118373 A1 | 5/2009 | Tripp et al. |

FOREIGN PATENT DOCUMENTS

| | | |
|---|---|---|
| DE | 2212148 | 9/1972 |
| DE | 3931147 | 3/1991 |
| DE | 19841615 | 3/2000 |
| EP | 0229022 | 7/1987 |
| EP | 0606599 A1 | 7/1994 |
| EP | 0681029 A2 | 11/1995 |
| EP | 1481671 | 12/2004 |
| EP | 1543834 | 6/2005 |
| EP | 1 938 828 | 7/2008 |
| GB | 2330076 | 4/1999 |
| JP | 52145509 | 12/1977 |
| JP | 58009084 | 2/1983 |
| JP | 59059623 | 4/1984 |
| JP | 363211219 | 9/1988 |
| JP | 04202138 | 7/1992 |
| JP | 6312924 | 11/1994 |
| JP | 07165583 | 6/1995 |
| JP | 07194351 | 8/1995 |
| JP | 8073369 | 3/1996 |
| JP | 08073369 | 3/1996 |
| JP | 9067245 | 3/1997 |
| JP | 09502202 | 3/1997 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2001161338 | 6/2001 |
| JP | 2002-12550 | 1/2002 |
| JP | 2002-505296 | 2/2002 |
| RU | 2045955 | 10/1995 |
| SU | 1247011 | 7/1986 |
| WO | WO 9507079 | 3/1995 |
| WO | WO 97/31630 | 9/1997 |
| WO | WO 9749405 | 12/1997 |
| WO | WO 99/44623 | 9/1999 |
| WO | WO 99/61038 | 12/1999 |
| WO | WO 00/68356 | 11/2000 |
| WO | WO 00/74696 | 12/2000 |
| WO | WO 02/02582 | 1/2002 |
| WO | WO 02/32234 | 4/2002 |
| WO | WO 03/000185 | 1/2003 |
| WO | WO 03/035007 | 5/2003 |
| WO | WO 03/068205 | 8/2003 |
| WO | WO 03/075943 | 9/2003 |
| WO | WO 03/082249 | 10/2003 |
| WO | WO 2004/037180 | 5/2004 |
| WO | WO 2004/062611 | 7/2004 |
| WO | WO 2005/039483 | 5/2005 |
| WO | WO 2005/084230 | 9/2005 |
| WO | WO 2006/053249 | 5/2006 |
| WO | WO 2006/062681 | 6/2006 |
| WO | WO 2007/021694 | 2/2007 |
| WO | WO 2007/067812 | 6/2007 |
| WO | WO 2009/124176 | 10/2009 |
| ZA | 200000857 | 8/2001 |

OTHER PUBLICATIONS

Bolick D et al., Endocrinology 144(12), pp. 5227-5231 (Dec. 2003).
Brown, et al. J. Chem. Soc. 545 (1959).
Buhler et al., Antioxidant Activities of Flavanoids, 3 pages, Nov. 2000.
Byrne, et al. J. Chem. Soc. (C):2810 (1971).
Carroccio, et al. Clin. Chem. 49(6):861-867 (2003).
Carson, J. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou et al. Eur. J. Biochem. 115:207-216 (1981).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al. J. Theor. Biol. 35:285-297 (1972).
Chou, J. Theor. Biol. 59:253-276 (1976).
Chou, et al., TIPS, pp. 450-454, Nov. 1983.
Cohen, Protein Kinases—the major drug targets of the twenty-first century? Nature Reviews, 1: 309-315 (2002).
Communication re EP 098253263 (Jan. 24, 2012).
Costa, et al. Digest. Liver Dis. 35:642-647 (2003).
Davies, WL. Abstract—Fertiliser, Feeding Stuffs and Farm Supplies J. 11:694 (1926).
De Keukeleire "Fundamentals of Beer and Hop Chemistry" Quimica Nova, 23(1) pp. 108-112 (2000).
Ding, et al. Biochem. Biophy. Res. Comm. 261:218-223 (1999).
European Examination Report for EP App. No. 02748188.6-1216 (Apr. 28, 2011).
European Search Report for EP App. No. 07809709.4 (Jan. 4, 2010).
European Search Report EP 05 723 839.6 (Jan. 22, 2010).
European Search Report EP 10006768 (Oct. 28, 2010).
European Search Report EP 10011254 (Jan. 31, 2011).
European Search Report EP 10013109 (Dec. 14, 2010).
European Search Report EP 10162893 (Sep. 14, 2010).
European Search Report for corresponding EP Application No. 02737562.5 (4 pages) (Dec. 14, 2004).

(56) References Cited

OTHER PUBLICATIONS

European Search Report for related European Application No. 02784313.5 (Nov. 27, 2006).
Exercise as Treatment for Arthritis, Rheumatic and Immunologic Diseases, Cleveland Clinic, www.clevelandclinic.org, Mar. 14, 2000.
Extended European Search Report EP 10162893.1 (Oct. 12, 2010).
Extended European Search Report EP 07717798.8 (Jun. 29, 2010).
Extended European Search Report EP 07809708.6 (Jan. 5, 2010).
Extended European Search Report EP08732208.7 (May 24, 2012).
Extended European Search Report EP06728126.5 (Feb. 16, 2012).
Examination Report re: New Zealand App. No. 581064 corresponding to PCT/US08/053803 (May 9, 2012).
Examination Report re: Australian App. No. 2006321727 corresponding to PCT/US06/047196 (May 5, 2011).
Examination Report re: Australian App. No. 2009231723 corresponding to PCT/US09/39272 (Jun. 26, 2012).
Fiebich et al., Effects to caffeine and paracetamol alone or in combination with acetylsalicylic acid on prostaglandin E2 synthesis in rat microglial cells; Neuropharmacology 39:2205-2213 (2000).
Foucault et al., J. Chromatography A 808(1-2):3-22 (May 29, 1998); abstract only (3 pages).
Friedman, et al. J Cutan Med. Surg. 6(5):449-459 (2002).
Gao et al., J. Food Sci. Nutr. vol. 9, pp. 240-244 (2004).
Gerhauser et al., Molecular Cancer Therapeutics vol. 1, No. 11, pp. 959-969 (2002).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Hariddradilepah 01, TKDL, Aug. 1, 1999, XP003024376, (3 pages).
Huang, et al. Cancer Res. 51:813-819 (1991).
Information on ArthroTrimTM product, downloaded from Internet Aug. 30, 2002.
Information on "Hops and Beer Flavours", IOB Technical Symposium, Apr. 2001, pp. 1-9.
Information on "Zyflamend and Zyflamend PM", downloaded from Internet Aug. 30, 2002.
International Search Report for Corresponding PCT Application No. PCT/US05/41018; 2pp (May 30, 2008).
International Search Report for PCT /US06/30920, Aug. 3, 2007, 3 pages (Aug. 30, 2007).
International Search Report for PCT/US02/19617 (Jun. 17, 2003).
International Search Report for PCT/US04/16043 (Jul. 27, 2005).
International Search Report for PCT/US06/47196 (Dec. 20, 2007).
Ivanovska et al., Study on the anti-inflammatory action of berberis vulgaris root extract, alkaloid fractions and pure alkaloids; in J. Immunopharmac., 18(10):553-561 (1996).
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-AH31.
Kanematsu, et al. J Bone Miner Res 12(11):1789-1796 (1997).
Konda, et al., Arthritis & Rheumatism 62(6): 1683-1692, (2010).
Kuo et al., Cancer Letter, 203:127-137 (2004).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. Of American Soc. For Experimental Biol., vol. 18, No. 4-5 (Jan. 1, 2004).
Lopes, Curr. Med Res Opin. 8(3):145-149 (1982).
Lukaczer et al., Phytotherapy Research, vol. 19, No. 10, pp. 864-869 (2005).
Mannering et al., Food, Nutrition and Chemical Toxicity X(X), pp. 311-323 (Jan. 1, 1993).
Meling, et al. Scand. J. Gastroenterol. 31:339-344 (1996).
Minich et al., Journal of nutrition and Metabolism, vol. 2010, article ID 467316, pp. 1-11, (2010).
Murvadyaghrtam, TKDL, Jan. 1, 2001, XP003024377 (4 pages).
Murvadyaghrtam, TKDL, Jan. 1, 1990, XP003024379 (4 pages).
Newark, et al., "Beyond Aspirin", pp. 147-151, Hohm Press (2000).
Noreen, et al. J. Nat. Prod 61:2-7 (1998).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/532,388 on Jun. 28, 2011.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 10/789,814 on Mar. 18, 2011.
Office Action issued in U.S. Appl. No. 11/344,555 on Jan. 19, 2011.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/636,867 on Aug. 30, 2010.
Office Action issued in U.S. Appl. No. 11/636,867 on Mar. 8, 2011.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 11/729,696 on Nov. 1, 2010.
Office Action issued in U.S. Appl. No. 11/820,600 on Sep. 30, 2010.
Office Action issued in U.S. Appl. No. 11/820,607 on Oct. 12, 2010.
Office Action issued in U.S. Appl. No. 12/030,335 on Oct. 21, 2010.
Office Action issued in U.S. Appl. No. 12/048,613 on Dec. 8, 2010.
Office Action issued in U.S. Appl. No. 12/754,820 on Mar. 15, 2011.
Office Action issued in U.S. Appl. No. 12/626,392 on Oct. 27, 2010.
Office Action issued in U.S. Appl. No. 11/729,696 on Mar. 25, 2010.
Office Action issued in U.S. Appl. No. 11/729,696 on Jul. 14, 2011.
Office Action issued in U.S. Appl. No. 11/820,755 on Oct. 18, 2010.
Office Action issued in U.S. Appl. No. 11/820,755 on Jun. 1, 2011.
Office Action issued in U.S. Appl. No. 10/464,410 on May 23, 2011.
Office Action issued in U.S. Appl. No. 11/820,607 on May 23, 2011.
Office Action issued in U.S. Appl. No. 11/820,653 on Aug. 8, 2011.
Office Action issued in U.S. Appl. No. 11/820,600 on May 26, 2011.
Office Action issued in U.S. Appl. No. 10/532,388 on Oct. 1, 2010.
Office Action issued in U.S. Appl. No. 11/501,393 on Nov. 9, 2011.
Office Action issued in U.S. Appl. No. 11/636,867 on Oct. 28, 2011.
Office Action issued in U.S. Appl. No. 12/626,392 on Jul. 8, 2011.
Office Action issued in U.S. Appl. No. 12/331,887 on Oct. 12, 2011.
Office Action issued in U.S. Appl. No. 12/754,820 on Nov. 30, 2011.
Office Action issued in U.S. Appl. No. 12/331,887 on Jul. 5, 2012.
Office Action issued in U.S. Appl. No. 12/634,877 on May 9, 2012.
Ohkura et al., Japanese Joural of Pharmacognosy, 44(3):171-175, (1990).
Pairet, et al. Inflamm. Res 47, Supplement 2S93-S101 (1998).
Panglisch, Monafsschrift fuer Brauwissen Schaft, 43(1), 4-16 (1990).
Parmar et al., Phytochemistry, vol. 28(2):591-593 (1989).
Parts per Milliion, 1 page, 2004.

(56) References Cited

OTHER PUBLICATIONS

Pippa, et al. Scand. J. Gastroenterol. Suppl. 167:32-35 (1989).
Plewig, et al. J Invest. Dermatol. 65(6):532-536 (1975).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Schmalreck et al, Canadian Journal of Microbiology, vol. 21:205-212 (1975).
Shah, et al. Gut 48:339-346 (2001).
Shimamura, et al. Biochem. Biophys. Res. Comm. 289:220-224 (2001).
Shureiqi, et al. Cancer Res. 6:6307-6312 (2001).
Sivri, Fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Subbaramaiah, et al. Cancer Res. 60:2399-2404 (2000).
Suh, et al. Cancer Res 58:717-723 (1988).
Supplemental European Search Report for EP 07845228.
Supplementary European Search Report form related EP Application No. 05851567, 8PP.
Supplementary Partial European Search Report for related European Patent Application No. 05723895.8, 5 pages (2007).
Supplementary European Search Report for EP Application No. EP 08729724, 9PP.
Supplementary European Search Report for EP Application No. EP 08859091, 5PP.
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tibble, et al. Gut 45:362-366 (1999).
Tiktakaghrtam, TKDL, Jan. 1, 1922, XP003024378 (1922).
Tobe, et al. Biosci. Biotech. Biochem 61(1):158-159 (1997).
Tripp et al., Hop and modified hop extracts have potent in vitro anti inflammatory properties; Proc. 1st IS on Humulus; Eds, K.E. Hummer et al.; Acta Hort. 668, ISHS 2005.
Turmeric: The Ayurvedic Spice of Life, published at www.bioponic.com/pdfs/TurmericAyurveda.pdf (2003).
US News and world report re Palliative Care, 10 pages (2008).
Van Cleemput, Hop (Humulus lupulus)-derived bitter acids as multipotent bioactive compounds; J. Nat. Prod. 72;1220-1230 (2009).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoecke et al., In Vivo, vol. 19, No. 1, pp. 103-107 (2005).
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Warner, et al. Proc Natl Acad Sci USA 96:7563-7568 (1999).
Wassel et al., Phytochemical examination and biological studies of Acacia . . . , Egyptian Journal of Pharaceutical Sciences, vol. 33 (1-2):pp. 327-340, 1992.
Written Opinion for corresponding PCT Application No. PCT/US05/41018; 3 pp (May 30, 2008).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26(6):753-760 (2003).
Zhao Feng et al., Biological and Pharmaceutical Bulletin, 26(1), pp. 61-65 (Jan. 2003).

ANTI-INFLAMMATORY CYCLOOXYGENASE INHIBITORS

CROSS-REFERENCE TO RELATED APPLICATIONS

This patent application is a continuation of U.S. application Ser. No. 10/008,778, filed Nov. 13, 2001, now U.S. Pat. No. 8,158,160, issued Apr. 17, 2012. The contents of the earlier application are hereby incorporated by reference as if recited herein in their entirety.

FIELD OF THE INVENTION

This invention relates to therapeutic compositions that exhibit anti-inflammatory properties and inhibit cyclooxygenase. The compositions are useful for treating osteoarthritis and rheumatoid arthritis, as well as pain related to connective tissue trauma or injury.

BACKGROUND OF THE INVENTION

Osteoarthritis is a degenerative joint disease and is the most common form of arthritis, affecting over 20 million people in America alone, most of which are 45 years old or older. Osteoarthritis causes the cartilage that covers the bone ends to deteriorate, causing pain, inflammation, and disability. Rheumatoid arthritis affects fewer people than osteoarthritis, nonetheless rheumatoid arthritis still affects just over 2 million people in the United States alone. There are also a large number of people who suffer from problems with connective tissue damaged by trauma or injury.

There is a real need for a faster onset of action for the quick relief of pain. Joint inflammation and pain such as that associated with osteoarthritis is the result of increased levels of pro-inflammatory prostaglandins that are derived from arachidonic acid via the enzyme cyclooxygenase. There are two types of this enzyme, COX-1 and COX-2. Non-steroidal anti-inflammatory drugs such as aspirin and ibuprofen reduce the pain and swelling of arthritis by inhibiting the COX-1 form of the enzyme, but have the side effect of causing gastric erosion if used on a regular basis. The newer arthritis drugs such as rofecoxib, and celecoxib, inhibit the COX-2 form of the enzyme, and reduce pain without causing a high incidence of gastric erosion.

In the early 1990s, an inducible isoform of cyclooxygenase (COX) was found. This paved the way for the discovery that COX exists in at least two isoforms; a constitutive "house keeping" form of the enzyme, COX-1, which is responsible for homeostatic functions, and an inducable isoform, COX-2, associated with inflammatory conditions and mitogenic events.

Non-steriodal anti-inflammatory drugs (NSAIDs) such as aspirin, provide pain relief during inflammation by reducing COX-2, but at the expense of also inhibiting the houskeeping or homeostatic functions of COX-1. Part of these homeostatic functions include healing of ulcerations in the stomach, and certain cardiovascular benefits. The NSAIDs are more selective for the COX-1 form of the enzyme, and are thus referred to as COX-1 inhibitors. However, the COX-1 inhibitors also inhibit the COX-2 isoform.

The GI upset and stomach irritation caused by high doses of COX-1 inhibitors is due to their action on prostaglandin production in a manner similar to that of aspirin and aspirin-like anti-inflammatory agents. Numerous studies have shown that the relative incidence of these GI side effects can be correlated to the relative COX-2 specificity of these agents. The higher the specificity for COX-2 over COX-1, the lower the incidence of GI upsets. Accordingly, cyclooxygenase inhibiting agents with increased COX-2 specificity may provide improved anti-inflammatory compositions having less incidences of gastrointestinal distress or side effects.

However, too much selectivity for COX-2 over COX-1 may not be desirable. Certain side-effects may result from COX inhibitors that are extremely selective for COX-2. For example, the cardiovascular benefit of aspirin, a predominantly COX-1 non-steroidal anti-inflammatory drug (NSAID), is thought to be due to its activity as an anti-platelet aggregating drug. COX-2 inhibition does not result in anti-platelet aggregation. Current pharmaceutical COX-2 inhibitors, such as celecoxib or rofecoxib, are highly specific COX-2 inhibitors, and would not be expected to have any COX-1 inhibitory activity. Thus, the cardiac-related side effects that have been noted with the use of some COX-2 specific inhibitors may be related to the lack of any COX-1 inhibition while significantly inhibiting COX-2.

Furthermore, an additional problem associated with highly specific COX-2 inhibitors is the increase in gastric erosion produced by concurrent administration with other non-steroidal anti-inflammatory drugs (NSAIDS). For example, if a patient is taking a highly selective COX-2 inhibitor and also takes aspirin for cardiovascular benefit, the aspirin will cause even worse damage to the gastric mucosa. The reason for this is that some of the prostaglandins that are inhibited by cyclooxygenase inhibitors, such as prostaglandin E-2 (PGE2), are protective of the gastric mucosa, and actually contribute to healing of ulceration. Low dose aspirin produces small erosions in the stomach, and at the site of these ulcerations, the COX-2 enzyme becomes up-regulated. When COX-2 is blocked by selective COX-2 inhibitors, the protection afforded by the beneficial prostaglandins is eliminated. The result is that the ulcerative damage is made even worse. Concomitant administration of selective COX-2 inhibitors with aspirin is therefore contraindicated.

In summary, highly selective single entity COX-2 inhibitors such as rofecoxib and celecoxib, while important new drugs for the treatment of pain associated with osteoarthritis and other maladies, have some serious potential side-effects. These side effects can be divided into two major groups; 1) cardiovascular, and 2) worsening of gastric erosion when taken with aspirin or other NSAIDS. Both of these side effects are related to an unbalanced total inhibition of the COX enzyme, and therefor, virtually complete blocking of prostaglandin production. Because prostaglandins have both positive and negative functions in the body, their total inhibition is a double-edged sword. Furthermore, there is a significant overlap in the patient populations that take both aspirin for cardiovascular benefit, and a selective COX-2 inhibitor for pain. Most of these subjects primarily consist of the elderly population. There is a significant need for anti-inflammatory pain relief without the negative side effects of the NSAIDs or the selective COX-2 inhibitors. Such a composition would provide pain relief while also inhibiting platelet aggregation, and providing protection for the gastric mucosa through some gastroprotective or cytoprotective mechanism. These second generation COX-2 inhibitors would be selective enough to inhibit COX-2 over COX-1, but not so selective that they would result in the additional side effects mentioned above.

In the search for new anti-inflammatory compounds, many potential candidates have come from the plant kingdom. These botanicals are usually extracted and tested in-vitro for COX inhibition using various cell lines and methods. Usually these methods involve screening the compounds for COX-2 and COX-1 inhibition by measuring the inhibition of prostaglandin E-2 for COX-2 inhibition, and TxB2 for COX-1 inhibition. Selectivity can then be determined by calculating the COX-2/COX-1 ratio. But many of these compounds have limited bioavailability in the human or animal gastrointestinal tract. Thus lack of good absorption into the blood stream limits the therapeutic effects of these compounds due to low plasma levels of the active principles.

Part of the poor absorption of botanical COX inhibitors is due in turn to low solubility of these compounds in biological fluids. The pH of the stomach in humans is about 1.2, and in the small intestine, it rises to about pH7.5. Compounds must be somewhat soluble in acidic conditions to provide a fast onset of action. While most compounds are absorbed in the small intestine, they must undergo dissolution and go into solution before they can be absorbed into the blood stream. Ideally, for fast onset of action, a compound should start undergoing dissolution while still in the stomach, and continue dissolution during transit in the small intestine. The compound should therefore be somewhat soluble in the acidic pH of the stomach, as well as the more basic "buffer" conditions that exist in the small intestine.

When screening botanical extracts for COX inhibition in-vitro, a solution of the compound must be made up which is added to the media containing the cells and the other substances. This solution is usually prepared over a range of different concentrations, so that a dose response curve can be calculated. To create a solution of a compound with limited solubility in physiological fluids, a solvent is usually employed. The most commonly used solvent is DMSO, or dimethylsulfoxide, which is somewhat of a universal solvent. But this method produces an artifact that is related to the artificial conditions in which the compound has been put into solution. The fluids in the gastrointestinal tract do not contain solvents such as DMSO or methanol. Many of these botanical compounds are not soluble in water, simulated gastric fluid, or simulated intestinal fluid. One therefore must make a leap of faith when extrapolating these in-vitro results to in-vivo conditions.

It would be desirable to find compounds that exhibit good selective COX-2 inhibition in-vitro, that also have better solubility in physiological fluids. Such compounds would also result in better bioavailability, faster onset of action, and more effective pain relief with less side-effects.

What are needed are compositions and methods that address the problems noted above.

SUMMARY OF THE INVENTION

In an aspect, the invention relates to a pharmaceutical composition comprising a therapeutic quantity of a COX-2 inhibitor having an IC50-WHMA COX-2/COX-1 ratio ranging from about 0.23 to about 3.33. In an additional aspect of the invention, such compounds would also have better solubility in gastrointestinal fluids, over a wide range of pH. Another feature of the invention would be faster onset of action for pain relief or analgesic effects, and less gastrointestinal and cardiovascular side effects. Additionally, a further aspect of the invention would be the ability of patients to use low dose aspirin therapy for cardiovascular benefit in conjunction with the use of the pharmaceutical compositions described herein, with reduced gastric erosion.

DETAILED DESCRIPTION OF THE INVENTION

The inventor has unexpectedly discovered that the above noted problems can be solved by a pharmaceutical composition comprising a therapeutic quantity of a COX-2 inhibitor having an IC50-WHMA COX-2/COX-1 ratio ranging from about 0.23 to about 3.33 COX-2 inhibitors having an IC50-WHMA COX-2/COX-1 ratio more than about 3.33 may exhibit undesirable cardiovascular and gastrointestinal side effects. Furthermore, such a compound should preferably be soluble in physiological fluids, over a pH range of 1.2 to 10.

The COX-2 inhibitors useful in the practice of this invention (the "recited COX-2 inhibitors") may be obtained from a variety of sources, so long as the recited COX-2 inhibitor has an IC50-WHMA COX-2/COX-1 ratio ranging from about 0.23 to about 3.33. This may be obtained, for example, by mixing together two or more COX-2 inhibitors so as to arrive at an average IC50-WHMA COX-2/COX-1 ratio in the range from about 0.23 to about 3.33.

Preferably, the benefits of the invention may accrue if the recited COX-2 inhibitor is a botanical COX-2 inhibitor. In a especially preferred embodiment, the botanical COX-2 inhibitor comprises hops (*Humulus lupus* L). This botanical extract contains numerous compounds that may work in concert to produce anti-inflammatory effects while minimizing negative cardiovascular and gastrointestinal side-effects. Even more preferable, is an isomer of alpha acid resins contained in hops extract, or iso-alpha acids.

Hops has been in use by the beer industry for hundreds of years. Hops may exhibit some metabolic and endocrine effects. There at least six flavonoids that can be isolated from hops, and some of these flavonoids have antiproliferative and cytotoxic effects. The phytoestrogens in hops have also been shown to inhibit growth of human breast cancer cells. The unique flavonoid compounds isolated from hops therefore have potential as cancer chemopreventative agents by effecting the metabolism of carcinogens. Hops also exhibits antimicrobial properties.

The anti-inflammatory properties of hops extract has been traced to one of the bitter principles or resins in hops called humulone. Humulone is designated an alpha acid by the brewing industry. In one study, humulone inhibited arachidonic acid-induced inflammatory ear edema in mice (Yasukawa, K et al. Oncology 1995, March; 52(2): 156-158), and also inhibited skin tumor formation following initiation with a chemical challenge. Humulon, the alpha acid contained in hops, has also been shown to suppress cyclooxygenase-2 induction at the level of transcription (Yamamoto K, et al, FEBS Lett 2000 January 14, 465(2-3: 103-106). Humulon, therefor, could be considered a COX-2 inhibitor. Furthermore, humulon suppressed the TNFalpha-dependent cyclooxygenase-2 induction with an IC(50) of about 30 nM, a fairly low concentration.

Extraction of hops yields various essential oils, oleoresins, and alpha and beta acids. The primary alpha acids contained in hops are humulone, cohumulone, hulupone, adhumulone, and xanthohumols. The primary beta acids in hops are lupulone, colupulone, and adlupulone. The beta acids in hops are essentially insoluble in water.

The alpha acids in hops extract are not soluble at low pH. For example, the pH of gastric fluid is about 1.2, and at this pH, the alpha acids in hops such as humulone are not soluble. Even at the higher pH of the small intestine, which is about 7.5, the alpha acids are only sparingly soluble. The bioavailablilty of the alpha acids in the gastrointenstinal tract, will be very low due to the low solubility, and this will effect the onset of pain relief as well as the efficacy of the primarily COX-2 inhibition activity. The alpha and beta acids in hops in their native form, or as extracted by either solvent based or supercritical carbon dioxide, will exhibit very low bioavailability in-vivo.

When tested for COX-2 inhibition activity in-vitro, hops extract must be dissolved in a solvent such as DMSO. This solution is then subjected to testing in the various cell line models employed as described in Brooks, P et al, Interpreting the clinical significance of the differential inhibition of cyclooxygenase-1 and cyclooxygenase-2, Rheumatology 1999; 38: 779-788. In this article, it mentions the possibility that the IC50 of a COX-2 inhibitor may be higher than the plasma concentrations of the drug that are achieved clinically. In-vitro IC50 values may be meaningless if the bioavailability of the compound in-vivo does not produce high enough concentrations in plasma.

One of the discoveries of this invention is directed to a composition that results in more soluble and bioavailable formulations of hops by converting the alpha acids to iso-alpha acids, preferably the alpha acid humulone to iso-humulone. The iso-alpha acids are better in-vivo COX inhibitors with a COX-2 selectivity and side-effect profile that is superior to the same dose of unisomerized hop extract. The iso-alpha acids are therefore more effective for pain relief from osteoarthritis or trauma induced pain or inflammation. The major iso-alpha acids are trans-isocohumulone, trans-isohumulone and trans-isoadhumulone. There are also tetrahydroiso-alpha acids, hexahydroiso-alpha acids, p-iso-alpha acids.

The alpha acids in hops extract can be isomerized by heating the high viscosity extract with potassium hydroxide or another mineral salt in aqueous solution. The resulting hops extract yields primarily iso-alpha acids, which are more soluble at the pH of the human or animal gastrointestinal tract, and most importantly, the iso-alpha acids are more soluble during the early stage of dissolution in gastric and intestinal fluids, when the fast onset of action leading to pain relief is needed.

At pH 2 or below, the solubility of the alpha acids in hops is essentially zero. At pH 3-4 the alpha acids are only sparingly soluble, for example, a solution of only 100 ppm is possible at a pH of 4. At pH 6, only a 1-2% solution can be made, and at pH 10 about a 10% solution is possible. As mentioned before, the beta acids are virtually insoluble at low pH. However, iso-alpha acid is much more soluble at low pH as well as high pH. For example at pH 7.5 a 20% aqueous solution can be made of iso-alpha acid, whereas only a 10% solution can be made of alpha acid. A 30% aqueous solution can be made by incorporation of potassium hydroxide in heated distilled water to bring the pH up to 9. The iso-alpha acids are therefore at least 100% more soluble and available at the pH of the human small intestine, and even more soluble at the pH of the stomach, which is about 1.2. Neither the alpha acids or the beta acids are soluble at the pH of the stomach. Thus, the iso-alpha acids will exhibit greater absorption and faster onset of action because they will become available for absorption early on, because their dissolution will start to occur in the stomach and continue as they move into the small intestine. This will result in better availability in the proximal small intestine, and throughout the mid and distal small intestine, where most drugs are absorbed.

Hops resin is obtained from the yellow vesicles in the flowers of the hops plant. Extraction of hops resin is usually done using accepted, extraction techniques with such solvents as hexane or ethyl alcohol, which concentrates the alpha and beta acids.

A more preferred extraction technique is using liquid carbon dioxide under supercritical conditions can be used to separate the alpha and beta fractions. Supercritical fluid technology is a more recent and superior means of extracting and concentrating the active principles that are contained in botanical extracts. Furthermore, supercritical fluid extraction is not a solvent based system, so it results in solvent free extractions, and is less harmful to the environment, because there is no need to evaporate toxic organic solvents. $CO_2$ is the most commonly used material in supercritical fluid extraction and fractionation. Supercritical $CO_2$ extraction also allows for better separation and fractionation of certain components in hops that may not be necessary for a particular application, such as the elimination of estrogenic components which may not be needed in an anti-inflammatory formula. For instance, ethanol extracts of hops are known undesirably to possess strong estrogenic properties. These polyphenols are not soluble in carbon dioxide.

In-vitro testing or screening of the recited COX-2 inhibitors can be conducted by measuring the inhibition of prostaglandin E-2, a pro-inflammatory prostaglandin. This results in the calculation of the IC50 values, or the amount or concentration of the compound needed to inhibit COX-2 by 50%. This model measures the production of prostaglandin E2 (PGE2) by the COX-2 enzyme related pathways, when stimulated by LPS in an in-vitro cell line model. However, the human whole blood assay has been deemed the method of choice by a panel of experts for assessing and screening COX inhibitors (Brooks, P et al, Interpreting the clinical significance of the differential inhibition of cyclooxygenase-1 and cyclooxygenase-2, Rheumatology; 1999; 38: 779-788). Such assays are now considered to represent a more complete in-vitro picture of COX-2/COX-1 selectivity and potency. A modified version of the human whole blood assay called the William Harvey Modified Human Whole Blood Assay has been selected as one of the best models for testing the compositions described herein. To determine the COX-2/COX-1 inhibitory activity according to the invention, the William Harvey Modified Human Whole Blood/Cell Assay (WHMA) is used, as set forth in T. D. Warner et al., *Nonsteroid drug selectivities for cyclo-oxygenase-1 rather than cyclo-oxygenase-2 are associated with human gastrointestinal toxicity: A full in vitro analysis*, Proc. Natl. Sci. USA 96:7563-68 (1999), hereby incorporated by reference in its entirety. The results from this assay are used to calculate the IC50-WHMA COX-2/COX-1 ratio, which is simply the numerical ratio of the COX-2 IC50 divided by the COX-1 IC50 ratio, obtained using the WHMA.

An example of two highly selective COX-2 inhibitors that are currently approved by the U.S. Food and Drug Administration are rofecoxib and celecoxib. The IC50 for COX-2 according to the WHMA for these two drugs is 0.31 and 0.34 uM respectively. The IC 50 for COX-1 inhibition for rofecoxib is 63 uM and the COX-1 inhibition for celecoxib is 1.2 uM by the WHMA method. The IC50-WHMA COX-2/COX-1 ratio for these two drugs is therefore 0.3 for celecoxib and 0.0049 for rofecoxib Preferable doses of the recited COX-2 inhibitor range from about 5 mg. to about 1000 mg of the recited COX-2 inhibitor in the inventive compositions.

Dosage forms comprising according to the invention may be taken numerous times during the day or may be incorporated into sustained-release formulations to enable a single daily or nightly dose. Such sustained-release formulations provide for more effective suppression of pro-inflammatory prostaglandins due to cumulative inhibition. In addition, sustained-release formulations provide long lasting pain relief. Useful dosage forms include without limitation oral forms such as tablets, capsules, beads, granules, aggregates, powders, gels, solids, semi-solids, and suspensions. Lotions, transdermal delivery systems, including dermal patches, aerosols or nasal mists, suppositories, salves and ointments are also useful.

A variety of additives can be incorporated into the inventive compositions for their intended functions. These additives are usually used in small amounts.

Useful additives include, for example, gelatin, vegetable proteins such as sunflower protein, soybean proteins, cotton seed proteins, peanut proteins, rape seed proteins, blood proteins, egg proteins, acrylated proteins; water-soluble polysaccharides such as alginates, carrageenans, guar gum, agar-agar, gum arabic, and related gums (gum ghatti, gum karaya, gum tragacanth), pectin; water-soluble derivatives of cellulose: alkylcelluloses, hydroxyalkylcelluloses and hydroxyalky lalkylcelluloses, such as methylcellulose, hydroxymethylcellulose, hydroxyethylcellulose, hydroxypropylcellulose, hydroxyethylmethylcellulose, hydroxpropylmethylceflulose, hydroxbutylmethylcellulose, cellulose esters and hydroxyalkylcellulose esters such as: cellulose acetate phthalate (CAP), carboxyalky l celluloses, carboxyalkylalkylcelluloses, carboxyalkylcellulose esters such as carboxymethyl cellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVP/vinyl acetate copolymer, and polycrotonic acids, also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylan-finoethyl group, which may be quaternized if desired; and other similar polymers.

Processing aids such as sucrose, polydextrose, maltodextrin, lactose, maltose, stearic acid, microcrystalline cellulose, and the like may also be used. Examples of classes of additives include excipients, lubricants, oils, hydrocolloid suspending agents, buffering agents, disintegrating agents, stabilizers, foaming agents, pigments, coloring agents, fillers, bulking agents, sweetening agents, flavoring agents, fragrances, release modifiers, etc.

A useful composition according to the invention is a sustained-release composition comprising a sustained-release form of the recited COX-2 inhibitor. By providing the recited COX-2 inhibitor in sustained-release form, more effective inhibition of the cyclooxegenase enzyme is possible due to the accumulative manner in which the enzyme is inhibited. This will also prolong the duration of action for the active principles in the rectited COX-2 inhibitor. By providing a slow but constant release of active principles, levels of pro-inflammatory prostaglandin E-2 are kept reduced, thereby providing for long lasting pain relief, throughout the day or at night while asleep.

Sustained release within the scope of this invention can be taken to mean any one of a number of extended release dosage forms. The following terms may be considered to be substantially equivalent to sustained release, for the purposes of the present invention: continuous release, sustained release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.), hereby incorporated by reference.

The various sustained release technologies cover a very broad spectrum of drug dosage forms. Sustained release technologies include, but are not limited to physical systems and chemical systems. Physical systems include, but are not limited to, reservoir systems with rate-controlling membranes; microencapsulation; macroencapsulation; membrane systems; reservoir systems without rate-controlling membranes such as hollow fibers, ultra microporous cellulose triacetate, or porous polymeric substrates and foams; monolithic systems, including those systems physically dissolved in non-porous, polymeric, or elastomeric matrices (e.g., non-erodable, erodable, environmental agent ingression, and degradable); and materials physically dispersed in non-porous, polymeric, or elastomeric matrices (e.g., non-erodable, erodable, environmental agent ingression, and degradable); laminated structures, including reservoir layers chemically similar or dissimilar to outer control layers; and other physical methods, such as osmotic pumps or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous).

Hydrogels may also be employed as described in "Controlled Release Systems: Fabrication Technology", Vol. 11, Chapter 3; p 41-60; "Gels For Drug Delivery", Edited By Hsieh, D., incorporated by reference.

Sustained release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

Furthermore, compositions according to the invention may be administered or coadministered with conventional pharmaceutical binders, excipients and additives. Many of these are sustained-release polymers which can be used in sufficient quantities to produce a sustained-release effect. These include, but are not limited to, gelatin, natural sugars such as raw sugar or lactose, lecithin, mucilage, plant gums, pectin's or pectin derivatives, algal polysaccharides, glucomannan, agar and lignin, guar gum, locust bean gum, acacia gum, xanthan gum, carrageenan gum, karaya gum, tragacanth gum, ghatti gum, starches (for example corn starch or amylose), dextran, polyvinyl pyrrolidone, polyvinyl acetate, gum arabic, alginic acid, tylose, talcum, lycopodium, silica gel (for example colloidal), cellulose and cellulose derivatives (for example cellulose ethers, cellulose ethers in which the cellulose hydroxyl groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate, cross-linked sodium carboxymethylcellulose, cross-linked hydroxypropylcellulose, high-molecular weight hydroxymethylpropycellulose, carboxymethyl-cellulose, low-molecular weight hydroxypropylmethylcellulose medium-viscosity hydroxypropylmethylcellulose hydroxyethylcellulose, hydroxypropylcellulose, hydroxypropylmethylcellulose, sodium carboxymethylcellulose, alkylcelluloses, ethyl cellulose, cellulose acetate, cellulose propionate (lower, medium or higher molecular weight), cellulose acetate propionate, cellulose acetate butyrate, cellulose triacetate, methyl cellulose, hydroxypropyl cellulose, or hydroxypropylmethyl cellulose), fatty acids as well as magnesium, calcium or aluminum salts of fatty acids with 12 to 22 carbon atoms, in particular saturated (for example stearates such as magnesium stearate), polycarboxylic acids, emulsifiers, oils and fats, in particular vegetable (for example, peanut oil, castor oil, olive oil, sesame oil, cottonseed oil, corn oil, wheat germ oil, sunflower seed oil, cod liver oil, or high melting point hydrogenated vegetable oil such as can be produced from soy beans); glycerol esters and polyglycerol esters of saturated fatty acids $C_{12}H_{24}O_2$ to $C_{18}H_{36}O_2$ and their mixtures, it being possible for the glycerol hydroxyl groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other substances that may be used include: cross-linked polyvinyl pyrrolidone, carboxymethylamide, potassium methacrylatedivinylbenzene copolymer, high-molecular weight polyvinylacohols, low-molecular weight polyvinylalcohols, medium-viscosity polyvinylalcohols, polyoxyethyleneglycols, non-cross linked polyvinylpyrrolidone, polyethylene glycol, sodium alginate, galactomannone, carboxypolymethylene, sodium carboxymethyl starch, sodium carboxymethyl cellulose or microcrystalline cellulose; polymerizates as well as copolymerizates of acrylic acid and/or methacrylic acid and/or their esters, such as, but not limited to poly(methyl methacrylate), poly(ethyl methacrylate), poly(butyl methacylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), or poly(octadecyl acrylate); copolymerizates of acrylic and methacrylic acid esters with a lower ammonium group content (for example Eudragit® RS, available from Rohm, Somerset, N.J.), copolymerizates of acrylic and methacrylic acid esters and trimethyl ammonium methacrylate (for example Eudragit® RL, available from Rohm, Somerset, N.J.); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethylacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer, glutaminic acid/glutamic acid ester copolymer; carboxymethylethylcellulose glycerol monooctanoate; cellulose acetate succinate; polyarginine; poly(ethylene), poly(ethylene) low density, poly (ethylene) high density, poly(propylene), poly(ethylene oxide), poly (ethylene terephthalate), poly(vinyl isobutyl ether), poly(vinyl chloride) or polyurethane. Mixtures of any of the substances or materials listed herein may also be used in the practice of the invention.

The compositions according to the invention may be orally administered in a solid dosage form, or in a liquid dosage form such as a tea or soft drink. Soft gel capsules may also be employed. For the preparation of solutions or suspensions it is, for example, possible to use water, vegetable glycerine, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of drinkable solutions the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), gum acacia or other suspension agents selected from the hydrocolloids may also be used.

It is also possible to add preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

Furthermore, sustained release or immediate release compositions according to the invention may be administered separately, or may co-administered with other inventive sustained release or immediate-release biological equivalents or other therapeutic agents. Co-administration in the context of this invention is defined to mean the administration of more than one therapeutic in the course of a coordinated treatment to achieve an improved clinical outcome. Such co-administration may also be coextensive, that is, occurring during overlapping periods of time.

The pharmaceutical compositions of the present invention may be used to treat pain related to trauma of connective tissue in mammals; and may also be used to treat osteoarthritis, rheumatoid arthritis or acute pain. Dosing is by conventional means for the dosage selected. Conventional methods (such as dose ranging studies) may be used to determine dosage amounts; alternatively preferable dosage ranges have been disclosed elsewhere herein.

An advantage of the invention is that bioavailability, side effects profile, and onset of action of a recited COX-2 inhibitor can result in a synergistic increase in the analgesic activity of the composition. The mechanism by which this effect occurs is not certain, but may involve altered COX-2 inhibitor metabolism/pharmacokinetics, resulting in effective pain relief at a lower dose. For instance, the synergistic effect may increase the maximum concentration of the recited COX-2 inhibitor in the blood or blood plasma, or may prolong or enhance the bioavailability of the recited COX-2 inhibitor or its metabolites, or may impact other pathways that directly or indirectly interact with the pathways involving cyclooxygenase-2. In an embodiment, the conversion of hops extract to iso-alpha acids could result in a significantly increased analgesic effect from the hops component. Such a synergistic increase in the analgesic activity would be useful for inventive compositions for and methods of treating joint pain or other types of pain, including acute pain, or pain due to trauma or injury, or for improved inhibition of cyclooxygenase-2 in mammals.

Additionally, in another embodiment, the recited COX-2 inhibitor may be taken with aspirin without a worsening of gastric erosion from the aspirin. Likewise, subjects who are already taking the recited COX-2 inhibitor may also take daily low-dose aspirin therapy for cardiovascular benefit without major erosive damage to the gastric mucosa.

An advantage of the invention is that it provides an anti-inflammatory and pain relieving effect while reducing the danger of gastric erosion from frequent usage, such as would be encountered with a composition that did not comprise a recited COX-2 inhibitor. Still another benefit is the fast onset of pain relief action due to the immediate anti-inflammatory effects of the recited COX-2 inhibitor. Surprisingly, by converting the alpha acids in hops to iso-alpha acids, significantly more effective joint pain relief is achieved initially, as well as over time. Additionally, the use of iso-alpha acids contained in one of the preferred compounds also results in more effective reduction of pain than native hops extract or alpha acid that has not been converted to iso-alpha acid. In some cases, the botanical extract may be more effective than the isolated single chemical principle alone. This may translate into a reduction in dose amount, or an increase in the analgesic efficacy of the inventive pharmaceutical composition. Therefore, the inventive pharmaceutical composition may result in significantly greater analgesic effects than either ingredient alone. With respect to iso-alpha acids, the group of isomerized acids may be more effective than a single alpha acid such as iso-humulone.

EXAMPLE 1

Patients with moderate to severe pain requiring an oral analgesic/anti-inflammatory drug, can be administered iso-alpha acids (500 mg.) or a typical extract of hops containing 50% alpha and 25% beta acids (500 mg.) (virtually no iso-alpha acid). Typical pain models would include osteoarthritis, post operative pain, dysmenorrhea, post partum pain, or dental extraction pain. Crossover design or completely randomized design can be used. To determine analgesic efficacy, an observer will conduct interviews with the patients to determine the level of pain at various time points. Patients are asked to subjectively estimate the time at which the medication begins to provide significant relief. Patients are given a stopwatch to help estimate the onset of pain relief more accurately. Appropriate statistical methods can be used to show that the iso-alpha acids of hops have a shorter onset of action and greater degree of pain relief than the unisomerized hops extract.

EXAMPLE 2

Toxicity or side effect reduction can be tested according to the following method; Groups of 6-10 guinea pigs are dosed orally with either vehicle (glycerine), a standardized hops extract containing about 42% alpha acids and 20% beta acids (standardized in glycerine), and a solution containing 70% iso-alpha acids. Different doses are administered via different concentrations of the hops extracts in vehicle such that a dose response curve is possible. Within 24 hours after the dose, the animals are examined for gross abnormalities of the GI tract, particularily erosions of the gastric mucosa of the stomach. Microerosions and redness or ulcerations are noted, and the effects are compared between the treatment groups as described in Aberg et al; Acta Pharmacol. Toxicol. 28: 249-257, 1970. These observations indicate that the iso-alpha acid group has significantly less gastric erosion than the alpha acid group.

EXAMPLE 3

Solubility of a predominantly iso-alpha acid hops extract is compared to a generic extract containing primarily unisomerized alpha and beta acids in gastrointestinal fluids as follows; Simulated gastric fluid (SGF) and simulated intestinal fluid (SW) can be prepared according to USP, or as follows:

1. Alternative preparation of simulated gastric fluid (SGF) (pH 1.2)

Sodium chloride (2 g) and pepsin (3.2 g) are co-dissolved in 7.0 ml of hydrochloride acid. Deionized water is added to make the final volume equal to 1000 ml. pH should be 1.2. Pepsin activity of 800-2500 units per mg of protein is available from Sigma Chemical. Equilibrate to 37 degrees C.

2. Alternative Preparation of simulated intestinal fluid (SIF) (pH 7.5)

Monobasic potassium phosphate (23.8 g) is dissolved in 875 ml of water. Sodium hydroxide (665 ml, 0.2N) and 1400 ml of water are then added. Pancreatin (35 g) is added and the resulting solution is adjusted with 0.2N sodium hydroxide to a pH of 7.5+–0.5. The solution is diluted with water to a final volume of 3500 ml. Equilibrate to 37 degrees C.

Use basket method, and set rotation speed at 50 RPM and maintain dissolution media at 37 degrees C.

Sample points:

1 and 2 hours in simulated gastric fluid (SGF), drain and refill with SW.

3, 5 and 8 hours in simulated intestinal fluid (SW).

The iso-alpha acids, alpha acids, and beta acids were analyzed by HPLC according to the method described in; American Society of brewing Chemists. Report of Subcommittee on Analysis of Hop Bittering Constituents. Journal 37 (3): 112 (1979). This method utilizes reverse-phase high-performance liquid chromatography (HPLC) with ultraviolet detection to separate and quantitate cohumulone, n-+ad-humulone, colupulone, and n-+ad-lupulone as well as the various iso-alpha acids in hops and hops extracts. Samples are taken from each time point and analyzed. Substantially more iso-alpha acids are present in each sample than alpha acids. Virtually no beta acids are found at any time points. This is an indication that the iso-alpha acids are available for absorption starting in the stomach, as evidenced by the amount present in simulated gastric fluid, and in the small intestine, as evidenced by the amount available in simulated intestinal fluid when compared to the amount of unisomerized alpha acids from a generic hops extract.

EXAMPLE 4

COX-2 Inhibition

A supercritical $CO_2$ extract of hops that has been converted to 70% iso-alpha acids is dissolved in distilled water and potassium hydroxide to make up a solution of about 30% iso-alpha acids. A second sample of generic supercritical $CO_2$ hops extract containing 42% alpha acids is also prepared in water at a 10% solution, which was the maximum amount that would go into solution. Both solutions are verified by HPLC.

Each solution is tested according to the William Harvey Modified Human Whole Blood/Cell Assay, as set forth in T. D. Warner et al., *Nonsteroid drug selectivities for cyclo-oxygenase*-1 rather than *cyclo-oxygenase*-2 are associated with human gastrointestinal toxicity: A full in vitro analysis, Proc. Natl. Sci, USA 96:7563-68 (1999).

Human whole blood (8 concentrations, n=4) is collected of blood by venapuncture into heparin. For determining COX-1: Incubation of test compound(s) for 1 hour, with addition of stimulus (A23187) for 30 minutes. For COX-2: Incubation of test compounds for 1 hour, addition of stimulus (A23187) for 30 minutes. Following this, measure TxB2 by RIA (index of COX-1 activity); measure PGE2 by RIA (index of COX-2 activity). The results are expressed as % control, and COX-2/COX-1 ratio is calculated.

EXAMPLE 5

A 70% iso-alpha acid hops extract is dissolved in dimethylsulfoxide and its effect on cyclooxigenase 2 (COX-2) activity is measured using the 184B5/HER cell line as described by Zhai et. al. in Cancer Research, (1993), 53, 2272-2278. In this assay, if basal COX-2 activity is inhibited, production of prostaglandin E-2 (PGE2) is significantly reduced because the synthesis of PGE2 from arachidonic acid (sodium arachidonate is added to the medium) is blocked or reduced by the iso-alpha hops extract. PGE2 production released by cells can be measured by enzyme immunoassay (ELISA) and shown to be significantly reduced.

As an additional test, the above formulation can be used to determine inhibition of recombinant human COX-2 enzyme activity. In that model, radioactive arachidonic acid is added to a reaction mixture containing human recombinant COX-2 enzyme and other chemicals. Levels of prostaglandin E-2 are measured using high pressure liquid chromatography (FI-PLC). The percent activity is determined by comparing levels of synthesis of PGE2 in control incubations with levels seen in incubation mixtures containing known concentrations of test compounds.

EXAMPLE 6

A soft gelatin capsule is prepared by mixing a 70% iso-alpha acid extract of hops with glycerin and other suitable excipients. Soft gelatin capsules can be manufactured according to techniques known in the pharmaceutical sciences, by anyone skilled in the art with the corresponding equipment. Soft gelatin capsules can deliver a drug or therapeutic compound in the liquid state, and therefor have a fast onset of action. Soft gel capsules were prepared accordingly to deliver 300 mg of iso-alpha acids per capsule in a base of vegetable glycerin. 12 healthy subjects which are screened according to proper inclusion and exclusion criteria are administered two capsules per day (600 mg. of iso-alpha acids) for a period of 3 days. Included in the exclusion criteria is the stipulation that no subject was currently taking an NSAID or a COX-2 inhibitor. On the fourth day, each subject is instructed to take one baby aspirin consisting of 81 mg. of aspirin, in addition to the two capsules of ISO-alpha acids per day. This combination therapy is continued for another 2 days for a total of three days of combination therapy. Each subject is asked to fill out a subjective questionnaire related to experience of gastric discomfort. Such a questionnaire asks the patient to rate the degree of pain, discomfort, or dyspepsia according to a sliding scale of none, mild, or severe. In addition, each subject is subjected to endoscopic examination for gastric erosion. After a 2-week washout period, in which the subjects are instructed not to consume any NSAIDs or COX-2 inhibitors, the same subjects are instructed to take a typical dose of rofecoxib, a synthetic, highly selective COX-2 inhibitor, once per day for a period of three days. After three days, one baby aspirin (81 mg.) is also consumed concurrent with the rofecoxib dose as was done with the iso-alpha acids. The same questionnaire is used as was in the first part of the study, and the subjects are also examined by endoscopy for erosions of the gastric mucosa.

EXAMPLE 7

A 70% iso-alpha acid resin extract is produced by heating a standardized hop extract in aqueous solution with potassium hydroxide at a pH of 9. This high viscosity resin is placed in a jacketed high intensity mixer such as a Littleford W-10, which enables hot water or steam to be circulated around the vessel to elevate the temperature. To the resin is added a mixture of carriers consisting of modified corn starch, maltodextrin, and calcium silicate or silica. The high shear mixer blends the resin with the carriers at an elevated temperature and a dry free flowing powder is created. After cooling, hydrogenated soy oil with a melting point of 155 degrees F. is added at 2% by weight. The temperature of the mixer is increased by circulating hot water through the jacket of the mixer/reactor vessel, until the core temperature reaches the melting point of the oil, or about 160 degrees F. The powder is granulated with the molten oil and mixed thoroughly by the high intensity mixing blades which are capable of mixing at speeds up to 2000 RPM. The temperature is then reduced to about 70 degrees F. and the powder discharged. A free flowing, sustained-release powder is produced consisting of the following composition,

| | |
|---|---|
| Iso-alpha acids | 35% |
| Maltodextrin | 30% |
| Modified corn starch | 30% |
| Calcium silicate | 3% |
| Hydrogenated soy oil | 2% |

This powder can be used to fill two piece capsules, made into tablets, or combined with other ingredients in multi-component formulas for analgesic effect. The powder is more suitable for solid dosage forms other than soft gelatin capsules.

To enhance the onset of action for pain relief, it may be necessary to add a mineral salt or alkali earth salts such as magnesium hydroxide, aluminum hydroxide, potassium hydroxide, sodium hydroxide, or mineral carbonates such as calcium carbonate or sodium bicarbonate. However, some of these mineral salts may precipitate the iso-alpha acids, with unknown consequences. Potassium hydroxide is the preferred mineral salt because it does not form a precipitate with alpha acids or iso-alpha acids form hops. Therefore, combinations of iso-alpha acids with mineral salts or potassium hydroxide in various dosage forms suitable for oral consumption are preferred.

EXAMPLE 8

The dry powder produced during the first phase of example 7, prior to microencapsulation with hydrogenated vegetable oil, is blended with potassium hydroxide and encapsulated according to the following formula;
Each capsule contains:

| | |
|---|---|
| Iso-alpha acids dry powder (35% iso-alpha acids) | 500 mg. |
| Potassium hydroxide | 200 mg. |
| Magnesium Stearate | 3 mg. |
| Silica | 1 mg. |

While the present invention is described above in connection with the preferred or illustrative embodiments, those embodiments are not intended to be exhaustive or limiting of the invention, but rather, the invention is intended to cover any alternatives, modifications, or equivalents that may be included within its scope as defined by the appended claims.

The invention claimed is:

1. A method for treating osteoarthritis or rheumatoid arthritis in a mammal in need thereof comprising administering to the mammal a therapeutically effective amount of a composition consisting essentially of about 5 mg to about 1,000 mg per day of a compound selected from the group consisting of isohumulone, isocohumulone and isoadhumulone, wherein the composition is in an oral dosage form selected from the group consisting of tablets, hard shell capsules, soft gelatin capsules, beads, granules, aggregates, powders, gels, solids, and semi-solids.

* * * * *